United States Patent
Biris et al.

(10) Patent No.: US 8,697,181 B2
(45) Date of Patent: Apr. 15, 2014

(54) MULTIFUNCTIONAL $FE_3O_4$ CORED MAGNETIC-QUANTUM DOT FLUORESCENT NANOCOMPOSITES FOR RF NANO-HYPERTHERMIA OF CANCER CELLS

(75) Inventors: Alexandru S. Biris, Little Rock, AR (US); Yang Xu, Little Rock, AR (US); Daoyuan Wang, Little Rock, AR (US)

(73) Assignee: Board of Trustees of The University of Arkansas, Little Rock (AR)

( * ) Notice: Subject to any disclaimer, the term of this patent is extended or adjusted under 35 U.S.C. 154(b) by 197 days.

(21) Appl. No.: 13/072,416

(22) Filed: Mar. 25, 2011

(65) Prior Publication Data

US 2011/0237862 A1    Sep. 29, 2011

Related U.S. Application Data

(60) Provisional application No. 61/317,820, filed on Mar. 26, 2010.

(51) Int. Cl.
    *A61N 2/02*    (2006.01)

(52) U.S. Cl.
    USPC .................. 427/127; 977/774; 427/64

(58) Field of Classification Search
    USPC ............... 427/64, 127, 131, 212, 215, 220; 977/774
    See application file for complete search history.

(56) References Cited

U.S. PATENT DOCUMENTS

2008/0075957 A1*  3/2008  Kim et al. ............... 428/403
2009/0302304 A1* 12/2009  Peng et al. .................. 257/9

OTHER PUBLICATIONS

D. Thakur et al (Nanotechnologt 20(2009)485601, pp. 1-9).*
Peng, X. et al., Targeted magnetic iron oxide nanoparticles for tumor imaging and therapy, International Journal of Nanomedicine, 2008, 3, 311-321.
Lu, Y. et al., Modifying the surface properties of superparamagnetic iron oxide nanoparticles through sol-gel approach, Nano Letters, 2002, 2, 183-186.
Seo, W. et al., FeCo/graphitic-shell nanocrystals as advanced magnetic-resonance-imaging and near-infrared agents. Nature Materials, 2006, 5, 971-976.
Xu, Y. et al., Cobalt nanoparticles coated with graphitic shells as localized radio frequency absorbers for cancer therapy, Nanotechnology, 2008, 19, 435102-435111.
Pankhurst, Q.A. et al., Applications of magnetic nanoparticles in biomedicine, J. Phys. D: Appl. Phys., 2003, 36, R167-R181.
Kalambur, V.S. et al., In vitro characterization of movement, heating and visualization of magnetic nanoparticles for biomedical applications, Nanotechnology, 2005, 16, 1221-1233.

(Continued)

*Primary Examiner* — Michael Cleveland
*Assistant Examiner* — Tabassom Tadayyon Eslami
(74) *Attorney, Agent, or Firm* — Morris, Manning & Martin, LLP; Tim Tingkang Xia, Esq.

(57) ABSTRACT

A magnetic oxide-quantum dot nanocomposite and methods of synthesizing it. In one embodiment, the magnetic oxide-quantum dot nanocomposite has at least one magnetic oxide nanoparticle coated with a silica ($SiO_2$) shell and terminated with at least one thiol group (—SH), and at least one CdSe/ZnS quantum dot linked with the at least one $SiO_2$-coated magnetic oxide nanoparticle via the at least one thiol group. In one embodiment, the at least one magnetic oxide nanoparticle comprises at least one iron oxide ($Fe_3O_4$) nanoparticle.

12 Claims, 16 Drawing Sheets

(56) References Cited

OTHER PUBLICATIONS

Hergt, R. et al., Magnetic particle hyperthermia: nanoparticle magnetism and materials development for cancer therapy, J. Phys.: Condens. Matter, 2006, 18, S2919-S2934.

Bulte, J. et al., Iron oxide MR contrast agents for molecular and cellular imaging: NMR Biomedicine, 2004, 17, 484-499.

Kumar, R.V. et al., Preparation of amorphous magnetite nanoparticles embedded in polyvinyl alcohol using ultrasound radiation, J. Mater. Chem., 2000, 10, 1125-1129.

Corr S.A. et al., Multifunctional magnetic-fluorescent nanocomposites for biomedical applicatons, Nanoscale Res. Lett., 2008, 3, 87-104.

Yin, J.S. et al., Template-assisted self-assembly and cobalt doping of ordered mesoporous titania nanostructures, Adv. Mater., 1999.

Bruchez, M. et al., Semiconductor nanocrystals as fluorescent biological labels, Science, 1998, 281, 2013-2018.

Mattoussi, H. et al., Self-assembly of CdSe-ZnS quantum dot bioconugaes using an engineeed recombinant protein, J. Am. Chem. Soc., 2000, 122, 12142-12150.

Ballou, B. et al., Noninvasive imaging of quantum dots in mice, 2004, 15, 79-86.

Michalet, X, et al., Quantum dot for live cells, in vivo imaging, and diagnostics, Science, 2005, 307, 538-544.

Montet, X. et al., Imaging pancreatic cancer with a peptide-nanoparticle conjugate targeted to normal pancreas, Bioconjugate Chem., 2006, 17, 905-911.

Sun, Q. et al., Bright, multicolored light-emitting diodes based on quantum dots, Nature Photonics, 2007, 1, 717-722.

Blackman, B. et al., Bright and water-soluble near IR-emitting CdSe/CdTe/ZnSe Type-II/Type-I nanocystals, tuning the efficiency and stability by growth, Chem. Mater., 2008, 20, 4847-4853.

Woo, K. et al., Easy synthesis and magnetic properties of iron oxide nanoparticles, Chem. Mater., 2004, 16, 2814-2818.

Cheng, F.Y. et al., Characterization of aqueous dispersions of Fe3O4 nanoparticles and their biomedical applications, Biomaterials, 2005, 26, 729-738.

Yezhelyev, M.V. et al., Proton-sponge coated quantum dots for siRNA delivery and intracellular imaging, J. Am. Chem. Soc., 2008, 130, 9006-9012.

Gannon, C.J. et al., Intracellular gold nanoparticles enhance non-invasive radiofrequency thermal destruction of human gastrointestinal cancer cells, Journal of Nanobiotechnology, 2008, 6:2.

Fotakis, G. et al., In vitro cytoxicity assyas: comparison of LDH, neutral red, MTT and protein assay in hepatoma cell lines following exposure to cadmium chloride, Toxicol. Lett., 2006, 160, 171.

Derfus, A.M. et al., Probing the cytotoxicity of semiconductor quantum dots, Nano Lett., 2004, 4, 11-18.

Lee, S. et al., 2.45 GHz radiofrequency fields alter gene expression in cultured human cells, FEBS Lett., 2005, 579, 4829-4836.

Young, J.H. et al., Frequency/depth-penetration considerations in hyperthermia by magnetically induced currents, Electron Lett., 1980, 16, 358-359.

Xu, Y. et al., Carbon-covered magnetic nanomaterials and their application for the thermolysis of cancer cells, International Journal of Nanomedicine, 2010, 5, 167-176.

Little R.B. et al., On the dynamical ferromagnetic, quantum hall, and relativistic effects on the carbon nanotubes nucleation and growth mechanism, Journal of Magnetism and Magnetic Materials, 2008, 320, 540-547.

Ghobrial, I.M. et al., Targeting apoptosis pathways in cancer therapy, CA Cancer J Clin., 2005, 55, 178-194.

* cited by examiner

US 8,697,181 B2

MULTIFUNCTIONAL $FE_3O_4$ CORED MAGNETIC-QUANTUM DOT FLUORESCENT NANOCOMPOSITES FOR RF NANO-HYPERTHERMIA OF CANCER CELLS

CROSS-REFERENCE TO RELATED PATENT APPLICATION

This application claims the benefit, pursuant to 35 U.S.C. §119(e), of U.S. provisional patent application Ser. No. 61/317,820, filed Mar. 26, 2010, entitled "MULTIFUNCTIONAL $Fe_3O_4$ CORED MAGNETIC-QUANTUM DOT FLUORESCENT NANOCOMPOSITES FOR RF NANO-HYPERTHERMIA OF CANCER CELLS," by Alexandru S. Biris, Yang Xu, and Daoyuan Wang, which is incorporated herein by reference in its entirety.

Some references, if any, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates generally to magnetic oxide-quantum dot nanocomposites, more particularly, to methods of synthesizing magnetic oxide-quantum dot nanocomposites and application of magnetic nanoparticle-quantum dot nanocomposites for hyperthermia cancer treatments.

BACKGROUND

Pancreatic cancer is the fourth leading cause of cancer death in men and women worldwide. While the use of hyperthermia therapy in treating some other forms of cancer has been heavily researched, little has been known about the potential of the therapy in treating patients with pancreatic cancer. This is an aggressive form of cancer for which better treatments are urgently needed.

Therefore, a heretofore unaddressed need exists in the art to address the aforementioned deficiencies and inadequacies.

SUMMARY OF THE INVENTION

In one aspect, the present invention relates to a method of synthesizing magnetic oxide-quantum dot nanocomposites. In one embodiment, the method includes the steps of:
  producing a plurality of magnetic oxide nanoparticles;
  coating each of the plurality of magnetic oxide nanoparticles with a silica ($SiO_2$) shell terminated with at least one thiol group (—SH) via a sol-gel process;
  producing a plurality of mercaptopropionic acid (MPA)-coated CdSe/ZnS quantum dots;
  dissolving the plurality of MPA-coated CdSe/ZnS quantum dots in a liquid to form a first solution;
  combining the plurality of $SiO_2$-coated and thiol-terminated magnetic oxide nanoparticles with the first solution to form a second solution; and
  stirring the second solution for a first period of time such that a plurality of nanocomposites is formed, wherein each of the plurality of nanocomposites comprises: (i) at least one $SiO_2$-coated magnetic oxide nanoparticle, and (ii) at least one CdSe/ZnS quantum dot linked with the at least one $SiO_2$-coated magnetic oxide nanoparticle via the at least one thiol group.

In one embodiment, the plurality of magnetic oxide nanoparticles comprises a plurality of iron oxide ($Fe_3O_4$) nanoparticles.

In a further aspect, the present invention relates to one or more magnetic oxide-quantum dot nanocomposites made according to the method set forth above.

In another aspect, the present invention relates to a magnetic oxide-quantum dot nanocomposite. In one embodiment, the magnetic oxide-quantum dot nanocomposite has at least one magnetic oxide nanoparticle coated with a silica ($SiO_2$) shell and terminated with at least one thiol group (—SH), and at least one CdSe/ZnS quantum dot linked with the at least one $SiO_2$-coated magnetic oxide nanoparticle via the at least one thiol group.

In one embodiment, the at least one magnetic oxide nanoparticle comprises at least one iron oxide ($Fe_3O_4$) nanoparticle.

In yet another aspect, the present invention relates to a method of cancer treatment using magnetic oxide-quantum dot nanocomposites. In one embodiment, the method includes the steps of:
  delivering a plurality of magnetic oxide-quantum dot nanocomposites to a cancer cell, wherein each of the plurality of magnetic oxide-quantum dot nanocomposites comprises: (i) at least one magnetic oxide nanoparticle coated with a silica ($SiO_2$) shell and terminated with at least one thiol group (—SH), and (ii) at least one CdSe/ZnS quantum dot linked with the at least one $SiO_2$-coated magnetic oxide nanoparticle via the at least one thiol group; and
  subjecting the cancer cell with the plurality of magnetic oxide-quantum dot nanocomposites to a radio frequency induction for a period of time effective to cause the cancer cell to die.

In one embodiment, the at least one magnetic oxide nanoparticle comprises at least one iron oxide ($Fe_3O_4$) nanoparticle.

These and other aspects of the present invention will become apparent from the following description of the preferred embodiment taken in conjunction with the following drawings and their captions, although variations and modifications therein may be affected without departing from the spirit and scope of the novel concepts of the disclosure.

BRIEF DESCRIPTION OF THE DRAWINGS

The drawings described below are for illustration purposes only. The drawings are not intended to limit the scope of the present teachings in any way. The patent or application file may contain at least one drawing executed in color. If so, copies of this patent or patent application publication with color drawing(s) will be provided by the Office upon request and payment of the necessary fee.

DETAILED DESCRIPTION

Figure 1A:
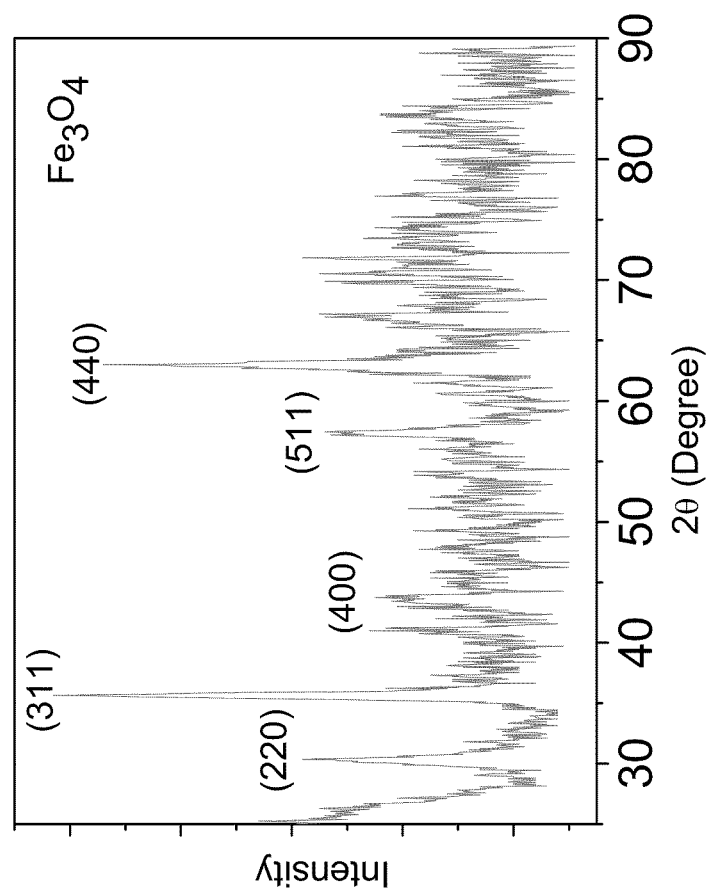
FIG. 1A shows an X-ray diffraction (XRD) pattern of the $Fe_3O_4$ nanoparticles according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, FIGS. 1-5, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "X-ray diffraction (XRD)" refers to one of X-ray scattering techniques that are a family of non-destructive analytical techniques which reveal information about the crystallographic structure, chemical composition, and physical properties of materials and thin films. These techniques are based on observing the scattered intensity of an X-ray beam hitting a sample as a function of incident and scattered angle, polarization, and wavelength or energy. In particular, X-ray diffraction finds the geometry or shape of a molecule, compound, or material using X-rays. X-ray diffraction techniques are based on the elastic scattering of X-rays from structures that have long range order. The most comprehensive description of scattering from crystals is given by the dynamical theory of diffraction.

As used herein, if any, the term "transmission electron microscopy (TEM)" refers to a microscopy technique whereby a beam of electrons is transmitted through an ultra thin specimen, interacting with the specimen as it passes through it. An image is formed from the electrons transmitted through the specimen, magnified and focused by an objective lens and appears on an imaging screen, a fluorescent screen in most TEMs, plus a monitor, or on a layer of photographic film, or to be detected by a sensor such as a CCD camera.

As used herein, if any, the term "energy dispersive X-ray spectroscopy (EDS or EDX)" refers to an analytical technique used for the elemental analysis or chemical characterization of a sample. It is one of the variants of X-ray fluorescence spectroscopy which analyzes X-rays emitted by the matter in response to being hit with charged particles such as electrons or protons, or a beam of X-rays. Its characterization capabilities are due in large part to the fundamental principle that each element has a unique atomic structure allowing X-rays that are characteristic of an element's atomic structure to be identified uniquely from one another.

As used herein, if any, the term "absorption spectroscopy" refers to spectroscopic techniques that measure the absorption of radiation, as a function of frequency or wavelength, due to its interaction with a sample. The sample absorbs energy, i.e., photons, from the radiating field. The intensity of the absorption varies as a function of frequency, and this variation is the absorption spectrum. Absorption spectroscopy is employed as an analytical chemistry tool to determine the presence of a particular substance in a sample and, in many cases, to quantify the amount of the substance present. Infrared and ultraviolet-visible (UV-Vis) spectroscopy are particularly common in analytical applications. The term "infrared spectroscopy" refers to absorption spectroscopy in the infrared spectral region; and the term "ultraviolet-visible (UV-Vis) spectroscopy" refers to absorption spectroscopy in the ultraviolet-visible spectral region.

As used herein, if any, the term "fluorescence spectroscopy" refers to a type of electromagnetic spectroscopy which analyzes fluorescence from a sample. It involves using a beam of light, usually ultraviolet light, that excites the electrons in molecules of certain compounds and causes them to emit light of a lower energy, typically, but not necessarily, visible light. It is a complementary technique to absorption spectroscopy.

As used herein, if any, the term "confocal microscopy" refers to an optical imaging technique used to increase optical resolution and contrast of a micrograph by using point illumination and a spatial pinhole to eliminate out-of-focus light in specimens that are thicker than the focal plane. In a conventional (i.e., wide-field) fluorescence microscope, the entire specimen is flooded evenly in light from a light source. All parts of the specimen in the optical path are excited at the same time and the resulting fluorescence is detected by the microscope's photodetector or camera including a large unfocused background part. In contrast, a confocal microscope uses point illumination and a pinhole in an optically conjugate plane in front of the detector to eliminate out-of-focus signal—the name "confocal" stems from this configuration. As only light produced by fluorescence very close to the focal plane can be detected the image optical resolution, particularly in the sample depth direction, is much better than that of wide-field microscopes. However as much of the light from sample fluorescence is blocked at the pinhole this increased resolution is at the cost of decreased signal intensity so long exposures are often required.

As used herein, if any, the term "hysteresis" refers to systems that have memory, where the effects of the current input (or stimulus) to the system are experienced with a certain delay in time. Hysteresis is well known in ferromagnetic materials. When an external magnetic field is applied to a ferromagnet, the atomic dipoles align themselves with the external field. Even when the external field is removed, part of the alignment will be retained: the material has become magnetized. The relationship between magnetic field strength (H) and magnetic flux density (M) is not linear in such materials. If the relationship between the two is plotted for increasing levels of field strength, it will follow a curve up to a point where further increases in magnetic field strength will result in no further change in flux density. This condition is called magnetic saturation. If the magnetic field is now reduced linearly, the plotted relationship will follow a different curve back towards zero field strength at which point it will be offset from the original curve by an amount called the remanent flux density or remanence. If this relationship is plotted for all strengths of applied magnetic field the result is a sort of S-shaped loop. The 'thickness' of the middle bit of the S describes the amount of hysteresis, related to the coercivity of the material.

As used herein, if any, the term "MTT assay" refers to colorimetric assay for measuring the activity of enzymes that reduce MTT to formazan dyes, giving a blue color. A main application allows to assess the viability (cell counting) and the proliferation of cells (cell culture assays). It can also be used to determine cytotoxicity of potential medicinal agents and toxic materials, since those agents would stimulate or inhibit cell viability and growth. MTT (3-(4,5-Dimethylthiazol-2-yl)-2,5-diphenyltetrazolium bromide, a yellow tetrazole), is reduced to blue formazan in living cells. A solubilization solution (usually either dimethyl sulfoxide, an acidified ethanol solution, or a solution of the detergent sodium dodecyl sulfate in diluted hydrochloric acid) is added to dissolve the insoluble purple formazan product into a colored solution. The absorbance of this colored solution can be quantified by measuring at a certain wavelength (usually between 500 and 600 nm) by a spectrophotometer. The absorption maximum is dependent on the solvent employed.

As used herein, if any, the term "LDH assay" or "LDH release assay" refers to colorimetric assay for the quantification of cell death and cell lysis based on the measurement of lactate dehydrogenase (LDH) activity released from the cytosol of damaged cells into the supernatant.

As used herein, "nanoscopic-scale," "nanoscopic," "nanometer-scale," "nanoscale," "nanocomposites," "nanoparticles," the "nano-" prefix, and the like generally refers to elements or articles having widths or diameters of less than about 1 µm, preferably less than about 100 nm in some cases. In all embodiments, specified widths can be smallest width (i.e. a width as specified where, at that location, the article can have a larger width in a different dimension), or largest width (i.e. where, at that location, the article's width is no wider than as specified, but can have a length that is greater).

As used herein, "plurality" means two or more.

As used herein, the terms "comprising," "including," "carrying," "having," "containing," "involving," and the like are to be understood to be open-ended, i.e., to mean including but not limited to.

OVERVIEW OF THE INVENTION

Magnetic nanoparticles such as iron oxide (IO, magnetite, $Fe_3O_4$)[1] and carbon covered Fe, Co or other ferromagnetic metals [2,3] are especially attractive for in vivo medical treatments since they can interact with induced electromagnetic fields of various frequencies so that they can penetrate a wide range of materials including bodily tissues. This property allows the particles to be manipulated, tracked, imaged and remotely heated [4,5]. These unique properties open up possibilities for their application in hyperthermic cancer treatments[3, 6, 7]. If magnetic nanoparticles are small enough (about 10 nm), they can demonstrate superparamagnetic behavior [8]. In addition, the reactivity of nanoparticles has been shown to greatly increase as their dimensions are reduced, and smaller particles may undergo rapid biodegradation when they are directly exposed to biological environments[9]. To solve these problems, the formation of a passive coating of inert materials such as silica on the surfaces of magnetic nanoparticles could help prevent their aggregation in blood vessels and improve their chemical stability [10]. Another advantage for the silica coating is that this surface is often terminated by a silanol group that can react with various coupling agents to covalently attach specific ligands which may bestow new properties on the particles. These include drug molecules, fluorescent compounds, biological agents, proteins, DNA, RNA, et al. [11-13]. The aspects of the present invention involve the association of magnetic IO and fluorescent quantum dots for the generation of nanocomposites that are thermally sensitive to RF radiation. The photoluminescent properties of QDs—narrow size-tunable emission, broad absorption, limited photobleaching and high brightness [14]—make them attractive alternatives to conventional organic fluorophores (such as the commercially available dyes) for life science research, because they are more stable and present reduced optical quenching. Quenching widely exists and the process is believed to occur due to fluorophore contact with the metal oxide particle surface, resulting in an energy transfer process. The problem can be partially resolved by providing the magnetic nanoparticle with a stable shell prior to the introduction of the fluorescent molecule, or by first treating the fluorophore with an appropriate spacer.

Pancreatic cancer is the fourth leading cause of cancer death in men and women worldwide [15]. While the use of hyperthermia therapy in treating some other forms of cancer has been heavily researched, little has been known about the potential of the therapy in treating patients with pancreatic cancer. This is an aggressive form of cancer for which better treatments are urgently needed. In this disclosure, it is shown that a novel two-in-one nanocomposite can act not only as a high efficiency RF absorber, but also can be used to label the apoptotic process of cancer cells. This functionalized nanocomposite has the potential to be used as a hyperthermal agent in pancreatic cancer therapy and other medical applications.

Highly biocompatible luminescent superparamagnetic nanocomposites have been synthesized from $Fe_3O_4/SiO_2$-QDs (IQ). $Fe_3O_4$ nanoparticles coated with a silica shell, $Fe_3O_4/SiO_2$ (IOS), and water soluble CdSe—ZnS Quantum Dots (QDs) were assembled together by the conjugation of an SH group. X-ray diffraction (XRD), transmission electron microscopy (TEM), Energy Dispersive X-Ray Analysis (EDX), UV-Vis absorption and emission spectroscopy and magnetometry were applied to characterize the nanocomposites. The nanocomposites exhibited multifunctional superparamagnetic and photoluminescent properties. Bright orange IQ nanoparticles were found to be successfully uptaken into pancreatic human cancer cells (Panc-1) after 24 h incubation. The IQ nanocomposites showed virtually no cytotoxicity towards the Panc-1 cells when the exposure concentration was below 50 µg/ml or 200 µg/ml as determined by MTT or LDH release measurements. After the inclusion of a very low dose (1.66 µg/ml) of florescent magnetic nanocomposites and exposure to a radio frequency (RF) treatment for only 2 minutes, most of the Panc-1 cells (99.2%) were found to be dead. The apoptosis process can be traceable due to the unique optical properties of the water soluble IQs. It was also confirmed that the structure-controlled IQ nanocomposites have reasonable magnetic properties, self-heating temperature rising characteristics, and high biocompatibility. This suggests that these IQ nanocomposites may be considered as bio-potential materials for applications involving in vivo nanohyperthermia and cancer treatment.

Thus, in one aspect, the present invention relates to a method of synthesizing magnetic oxide-quantum dot nanocomposites. In one embodiment, the method includes the steps of producing a plurality of magnetic oxide nanoparticles;

coating each of the plurality of magnetic oxide nanoparticles with a silica ($SiO_2$) shell terminated with at least one thiol group (—SH) via a sol-gel process;

producing a plurality of mercaptopropionic acid (MPA)-coated CdSe/ZnS quantum dots;

dissolving the plurality of MPA-coated CdSe/ZnS quantum dots in a liquid to form a first solution;

combining the plurality of $SiO_2$-coated and thiol-terminated magnetic oxide nanoparticles with the first solution to form a second solution; and stirring the second solution for a first period of time such that a plurality of nanocomposites is formed, wherein each of the plurality of nanocomposites comprises: (i) at least one $SiO_2$-coated magnetic oxide nanoparticle, and (ii) at least one CdSe/ZnS quantum dot linked with the at least one $SiO_2$-coated magnetic oxide nanoparticle via the at least one thiol group.

In one embodiment, the plurality of magnetic oxide nanoparticles comprises a plurality of iron oxide ($Fe_3O_4$) nanoparticles. The step of producing a plurality of magnetic oxide nanoparticles thus is performed by the steps of:

mixing a first amount of ammonium ferrous sulfate and a second amount of iron chloride to form a third solution;

adding a third amount of sodium hydroxide into the third solution to form a fourth solution;

stirring the fourth solution for a second period of time such that the plurality of iron oxide ($Fe_3O_4$) nanoparticles is formed; and isolating the plurality of $Fe_3O_4$ nanoparticles from the fourth solution.

In one embodiment, the step of stirring the fourth solution is performed under nitrogen protection.

In one embodiment, the step of isolating the plurality of $Fe_3O_4$ nanoparticles from the fourth solution is performed by using a magnet.

In one embodiment, the step of producing a plurality of mercaptopropionic acid (MPA)-coated CdSe/ZnS quantum dots is performed by the steps of:

dissolving a plurality of CdSe/ZnS particles in a first amount of chloroform to form a fifth solution;

adding a second amount of mercaptopropionic acid (MPA) to the fifth solution to form a sixth solution;

sonicating the sixth solution for a third period of time such that the plurality of MPA-coated CdSe/ZnS quantum dots is formed; and isolating the plurality of MPA-coated CdSe/ZnS quantum dots from the sixth solution.

In one embodiment, the third period of time is about 20 minutes.

In one embodiment, the step of isolating the plurality of MPA-coated CdSe/ZnS quantum dots from the sixth solution is performed via centrifugation and decantation. In one embodiment, the step of stirring the sixth solution is performed in a 35° C. water bath.

In one embodiment, the liquid is water.

In one embodiment, the first period of time is about 12 hours.

In one embodiment, the method further includes the step of isolating the plurality of nanocomposites from the second solution by using a magnet.

In a further aspect, the present invention relates to one or more magnetic oxide-quantum dot nanocomposites made according to the method set forth immediately above.

In another aspect, the present invention relates to a magnetic oxide-quantum dot nanocomposite. In one embodiment as shown in FIG. 2F, a magnetic oxide-quantum dot nanocomposite 200 has at least one magnetic oxide nanoparticle 200, which functions as a core, coated with a silica ($SiO_2$) shell 204 and terminated with at least one thiol group (—SH) 206, and at least one CdSe/ZnS quantum dot 208 linked with the at least one $SiO_2$-coated magnetic oxide nanoparticle via the at least one thiol group 206. A magnetic oxide-quantum dot nanocomposite 200 in general has one or more terminating thiol groups (—SH) 206, and corresponding one or more CdSe/ZnS quantum dots 208. A magnetic oxide-quantum dot nanocomposite 200 can interface with another one or more magnetic oxide-quantum dot nanocomposites 200 by forming one or more links 210 via corresponding terminating thiol groups (—SH) 206.

In one embodiment, the at least one magnetic oxide nanoparticle includes at least one iron oxide ($Fe_3O_4$) nanoparticle.

In one embodiment, the at least one magnetic oxide nanoparticle has a size of about 10 nm. The weight ratio between the at least one magnetic oxide nanoparticle and the at least one CdSe/ZnS quantum dot is about 20%. The silica ($SiO_2$) shell is about 4 nm thick.

In one embodiment, the at least one CdSe/ZnS quantum dot is coated with mercaptopropionic acid (MPA).

In one embodiment, the at least one CdSe/ZnS quantum dot has a size of about 5 nm.

In yet another aspect, the present invention relates to a method of cancer treatment using magnetic oxide-quantum dot nanocomposites. In one embodiment, the method includes the steps of:

delivering a plurality of magnetic oxide-quantum dot nanocomposites to a cancer cell, wherein each of the plurality of magnetic oxide-quantum dot nanocomposites comprises: (i) at least one magnetic oxide nanoparticle coated with a silica ($SiO_2$) shell and terminated with at least one thiol group (—SH), and (ii) at least one CdSe/ZnS quantum dot linked with the at least one $SiO_2$-coated magnetic oxide nanoparticle via the at least one thiol group; and subjecting the cancer cell with the plurality of magnetic oxide-quantum dot nanocomposites to a radio frequency induction for a period of time effective to cause the cancer cell to die.

In one embodiment, the at least one magnetic oxide nanoparticle includes at least one iron oxide ($Fe_3O_4$) nanoparticle.

In one embodiment, the weight ratio between the at least one magnetic oxide nanoparticle and the at least one CdSe/ZnS quantum dot is about 20%.

In one embodiment, the at least one magnetic oxide nanoparticle has a size of about 10 nm.

In one embodiment, the silica ($SiO_2$) shell is about 4 nm thick.

In one embodiment, the at least one CdSe/ZnS quantum dot is coated with mercaptopropionic acid (MPA).

In one embodiment, the at least one CdSe/ZnS quantum dot has a size of about 5 nm.

In one embodiment, the radio frequency induction has a frequency of about 350 kHz. The period of time ranges from about 2 minutes to about 10 minutes for a radio frequency induction of about 5 kW power.

In one embodiment, the plurality of magnetic oxide-quantum dot nanocomposites is dissolved in a solution prior to being delivered to the cancer cell.

In one embodiment, the plurality of magnetic oxide-quantum dot nanocomposites in the solution corresponds to a concentration of less than about 50 µg/ml.

In another embodiment, the plurality of magnetic oxide-quantum dot nanocomposites in the solution corresponds to a concentration ranging from about 0.83 µg/ml to about 1.66 µg/ml.

In one embodiment, the cancer cell is a pancreatic cancer cell. Additional details are set forth below.

EXAMPLES

Aspects of the present teachings may be further understood in light of the following examples, which should not be construed as limiting the scope of the present teachings in any way.

Example 1

Materials

Tetraethylorthosilicate (TEOS), 3-mercaptopropionic acid (MPA), 3-mercatopropyl-trimethoxysilane (MPS), ammonium ferrous sulfate (99.7%), iron chloride (99.0%), sodium hydroxide (96%), sodium citrate (98%), cadmium dichlorate (99.0%), selenium (99.95%), absolute ethanol (99.7%), ammonia (30 wt. %), zinc acetate (99.0%), sodium sulfide (98%), and acetone (99.5%) were all purchased from Aldrich and used as received unless otherwise noted.

Preparation of Iron-oxide Magnetic Nanoparticles

Iron-oxide (IO, $Fe_3O_4$) nanoparticles were synthesized as previously described[9]. Briefly, 5 mL of 0.5M ammonium ferrous sulfate and 10 mL of 0.5M iron chloride solution were mixed together. Then 15 mL of 3M sodium hydroxide solution was dropped into the solution under mechanical stirring and nitrogen protection. The additional sodium hydroxide kept a consistent concentration of hydroxide so as to obtain uniform nanoparticles. The resulting black precipitate was isolated with a magnet and washed with distilled water dozens of times until pH 7.0 was reached.

Synthesis of Dissoluble QDs

CdSe/ZnS quantum dots were synthesized according to previously published literature[16]. The particles were dissolved in a minimum amount of chloroform and treated with mercaptopropionic acid (MPA). The resulting mixture was sonicated for 20 minutes. The chloroform solution gradually became turbid as the original long hydrocarbon chain ligands were replaced by MPA. The MPA-coated QD precipitate was isolated via centrifugation and decantation. Excess MPA was further removed by washing the precipitate with chloroform followed by centrifugation. Finally, a $NaHCO_3$ solution was added to the precipitate, and the nanocrystals were then dissolved in water[17].

Synthesis of Magnetic/Fluorescent Nanocomposites

Before combining QDs with IO, a silica shell was coated onto the magnetic particles to form the $Fe_3O_4/SiO_2$ (IOS) structure by a sol-gel process. In a typical procedure, 0.6 g of IO nanoparticles were coordinated with citric acid ions and this magnetic liquid was directly coated with amorphous silica via the hydrolysis of a sol-gel precursor to form $Fe_3O_4/SiO_2$—SH.

At last, the functional nanoparticles were combined with CdSe/ZnS by thiol coordination. The water soluble QD solution was then added quickly to the $Fe_3O_4/SiO_2$—SH solution and the product was left to stir in a 35° C. water bath for 12 hours. Finally, orange particles could be separated with a magnet from the solution, indicating that nanocomposites (IQ) with magnetic IO particles and fluorescent QDs had been assembled successfully.

Example 2

X-ray Diffraction (XRD)

Powder $Fe_3O_4$ XRD data was recorded on a Bruker AXS D8 advanced diffractometer (Cu-Ka) in h/h geometry with a secondary monochromator. The patterns were recorded over $10°<2\theta<100°$. The results were analyzed with EVA software.

TEM and EDX Analysis

Transmission Electron Microscopy (TEM) and Energy Dispersive X-ray (EDX) analysis were collected on a JEM2100F TEM (JEOL INC.) with an acceleration voltage of 200 kV. For the analysis, NP powders were dispersed in 2-propanol and sonicated for 10 minutes. A few drops of the suspension were deposited on a TEM grid. This preparation was then dried and evacuated before analysis.

UV-Vis-NIR Spectroscopy and Fluorescence Spectroscopy

IO, QDs, and IQ nanomaterials were measured in a 10 mm path length quartz cells using a UV-Vis-NIR absorption spectrometer (Varian Cary) and a fluorescence spectroscope (Varian Cary Eclipse) at room temperature to record the spectra of the various solutions involved in the synthesis route.

Characterization of Magnetic $Fe_3O_4$ (IO) Nanoparticles

Figure 1B:
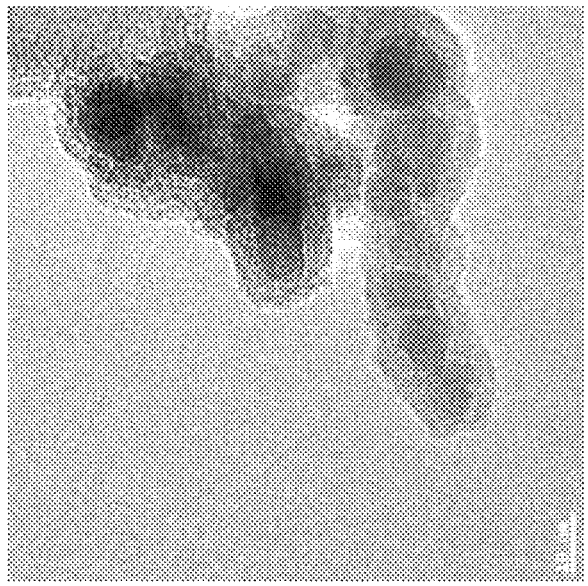
FIG. 1B shows a TEM image of the $Fe_3O_4$ nanoparticles according to one embodiment of the present invention.

FIG. 1A shows an X-ray diffraction (XRD) pattern of magnetic IO NPs. The pattern matches the same pattern for the magnetite ($Fe_3O_4$) phase as compared to standard XRD patterns reported elsewhere[18]. The sharp peaks that appeared approximately at $2\theta=30°$, $35°$, $43°$, $57°$ and $62°$ belonged to the $Fe_3O_4$ nanocrystalline structure [19]. FIG. 1B shows a TEM image of $Fe_3O_4$ nanoparticles. The $Fe_3O_4$ nanoparticles have an average size of about $10\pm0.3$ nm.

Figure 1C:
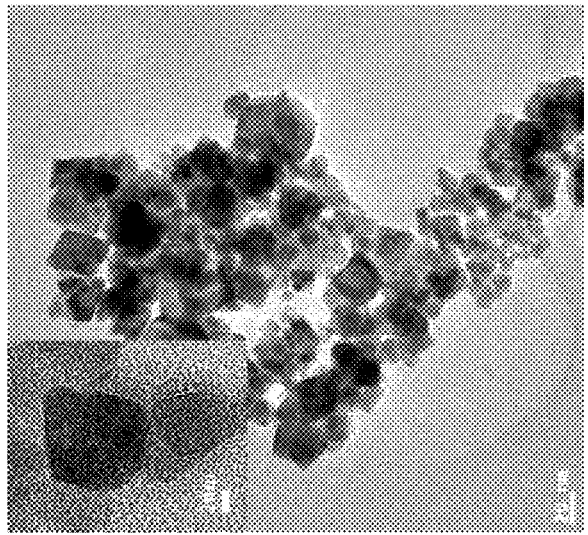
FIG. 1C shows a TEM image of the $Fe_3O_4$ nanoparticles covered with $SiO_2$ shells according to one embodiment of the present invention.

FIG. 1C shows a TEM image of the IO covered by $SiO_2$. The core-shell structure of the magnetic particles can be clearly observed. The concentration of TEOS precursors had a great effect on the thickness of the shell. Different thicknesses of silica shells resulted from different TEOS concentrations. In this study, 1.8 mmol/L of TEOS was used to form the $SiO_2$ shell with about a 4 nm thickness. The relative low concentration of TEOS was chosen as this helped retain the magnetic properties of the IO.

Characterization of QDs and $Fe_3O_4$-QDs (IQ) Nanocomposite

Figure 2A:
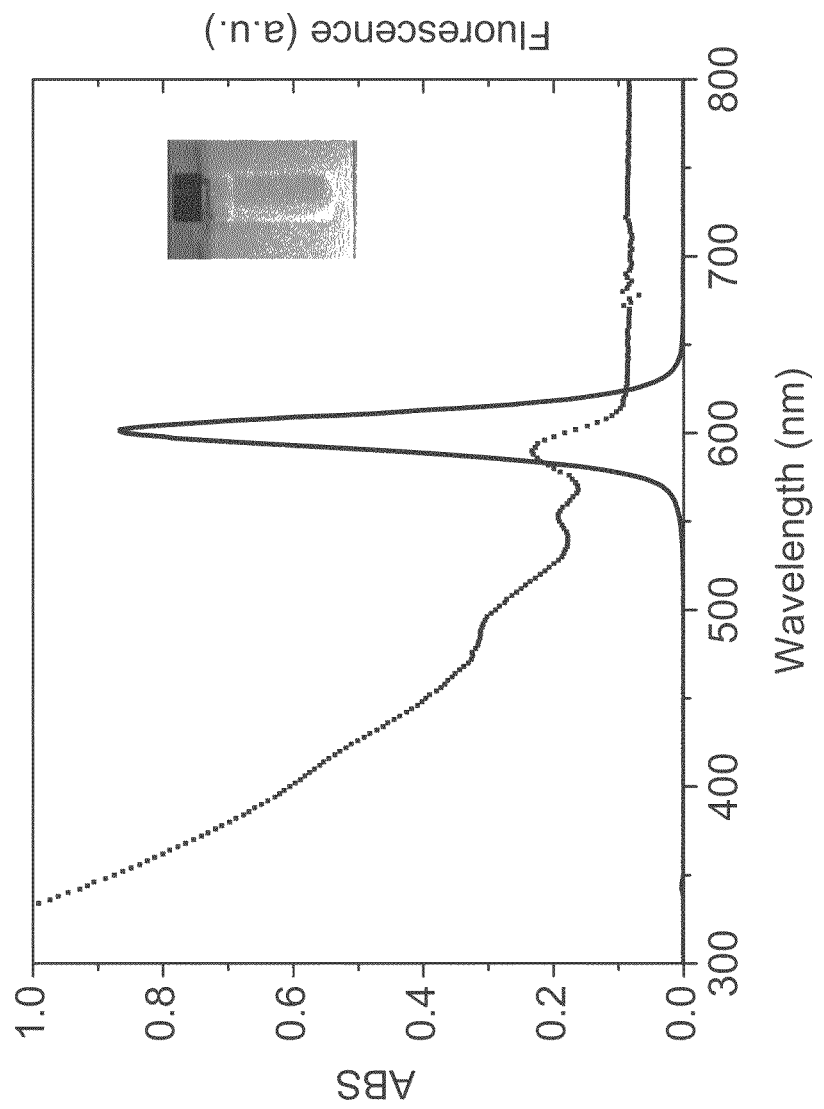
FIG. 2A shows an absorption spectrum (dotted line) and a fluorescence spectrum (solid line) of CdSe/ZnS quantum dots (QDs) according to one embodiment of the present invention. The insert shows a picture of the orange QD solution under UV radiation.
Figure 2B:
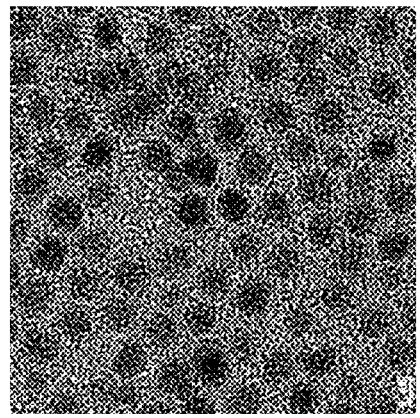
FIG. 2B shows a TEM image of CdSe/ZnS QDs according to one embodiment of the present invention.

FIG. 2A shows an absorption spectrum (dotted line) and a fluorescence spectrum (solid line) of CdSe/ZnS QDs dissolved in chloroform. The absorption spectrum shows an absorption peak at about 600 nm; the fluorescence spectrum shows an emission peak also at about 600 nm. The quantum yield reached as high as 30% when the Rhodamine B/ethanol solution (QY=0.95 in ethanol) was used as a comparative standard. FIG. 2B shows a TEM image of CdSe/ZnS QDs which confirms that the QDs have a very uniform size around 5 nm.

Figure 2C:
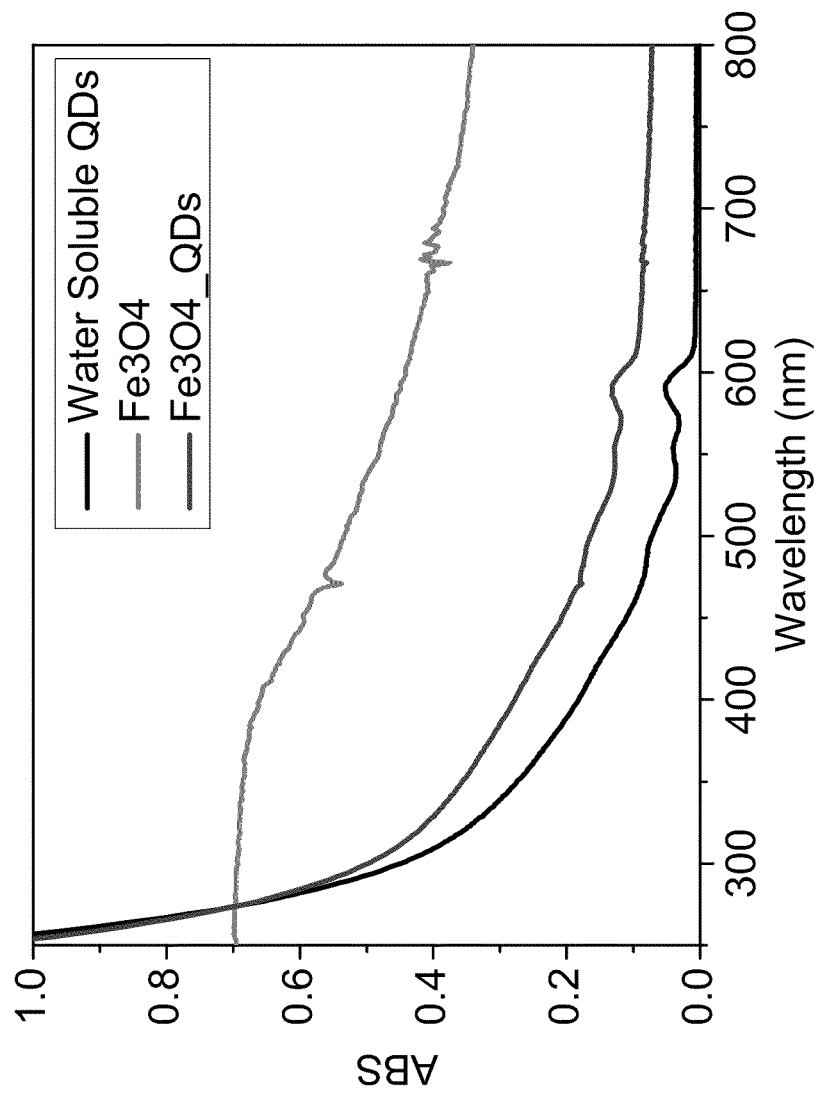
FIG. 2C shows absorption spectra of water soluble QDs (black line), $Fe_3O_4$ nanoparticles (red line), and $Fe_3O_4$-QDs (blue line), according to one embodiment of the present invention.

To achieve a high biocompatibility so that the particles may be used in bio-applications, the protective coatings of a QD should lead to the following properties: (i) stability (i.e. a lack of aggregation) in a biological environment; (ii) no significant non-specific surface adsorption of biomolecules onto the particles; and (iii) low cytotoxicity[20]. For these purposes, it is reasonable to manipulate the water miscibility and stability of the QDs first. In this study, QDs were functionalized by MPA and these can be dissolved in water and kept very stable for several months. FIG. 2C shows absorption spectra of water soluble QDs (black line), $Fe_3O_4$ nanoparticles (red line), and $Fe_3O_4$-QDs (IQ) (blue line). The MPA capped QDs also have excellent optical properties (as seen in the black curve in FIG. 2C) and narrow size distributions, with quantum yield values comparable to that of the original dots suspended in chloroform.

Figure 2D:
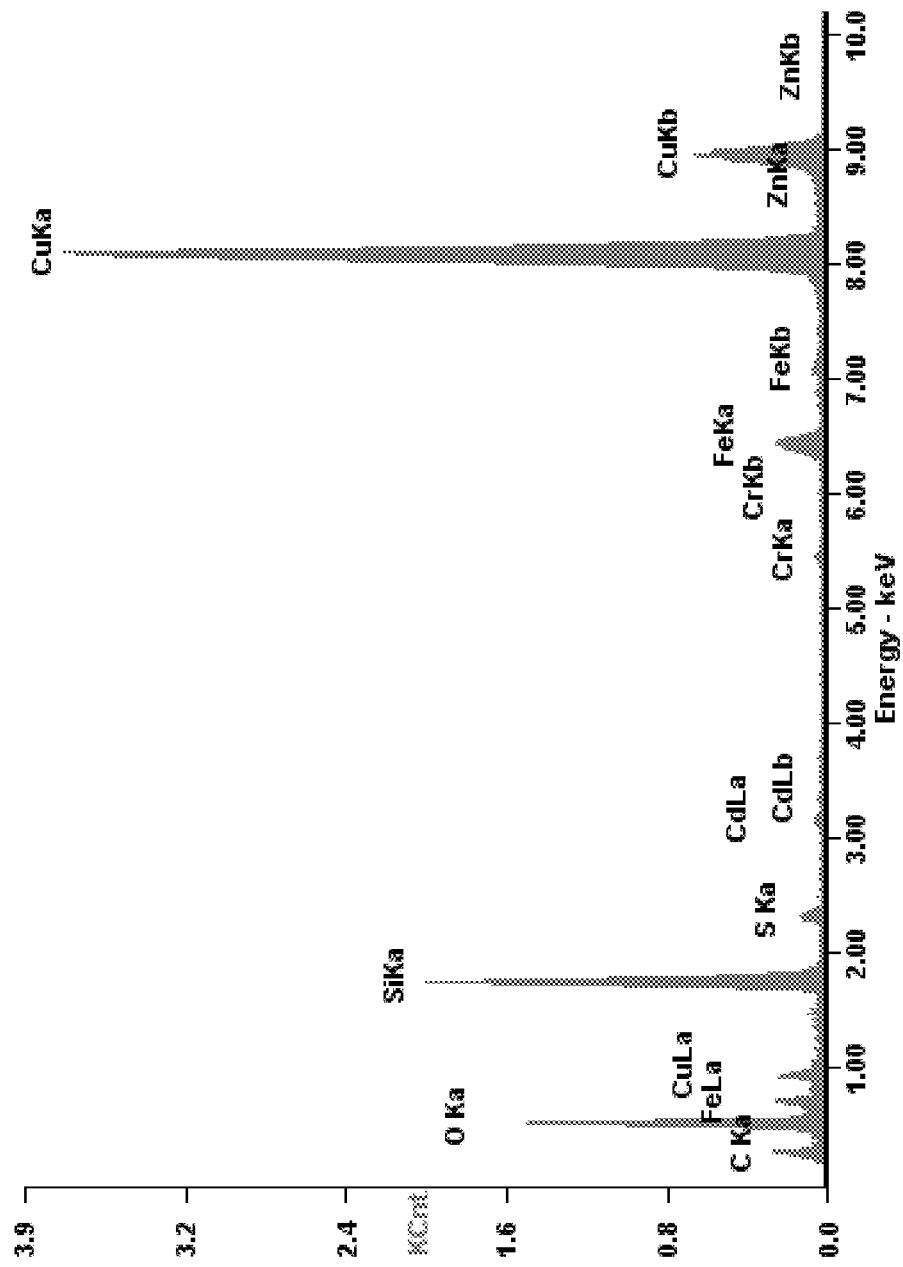
FIG. 2D shows an EDX spectrum of the $Fe_3O_4$—$SiO_2$/CdSe/ZnS nanocomposites according to one embodiment of the present invention.
Figure 2E:
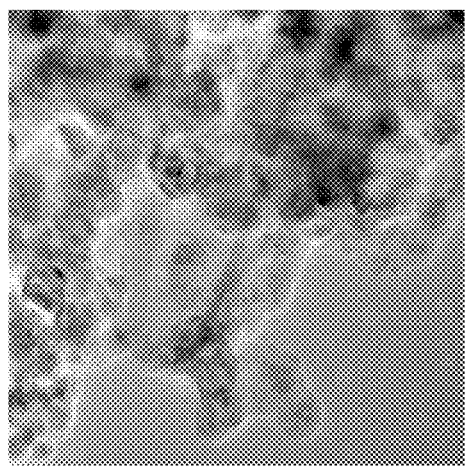
FIG. 2E shows a TEM image of the $Fe_3O_4$—$SiO_2$/CdSe/ZnS nanocomposites according to one embodiment of the present invention.
Figure 2F:
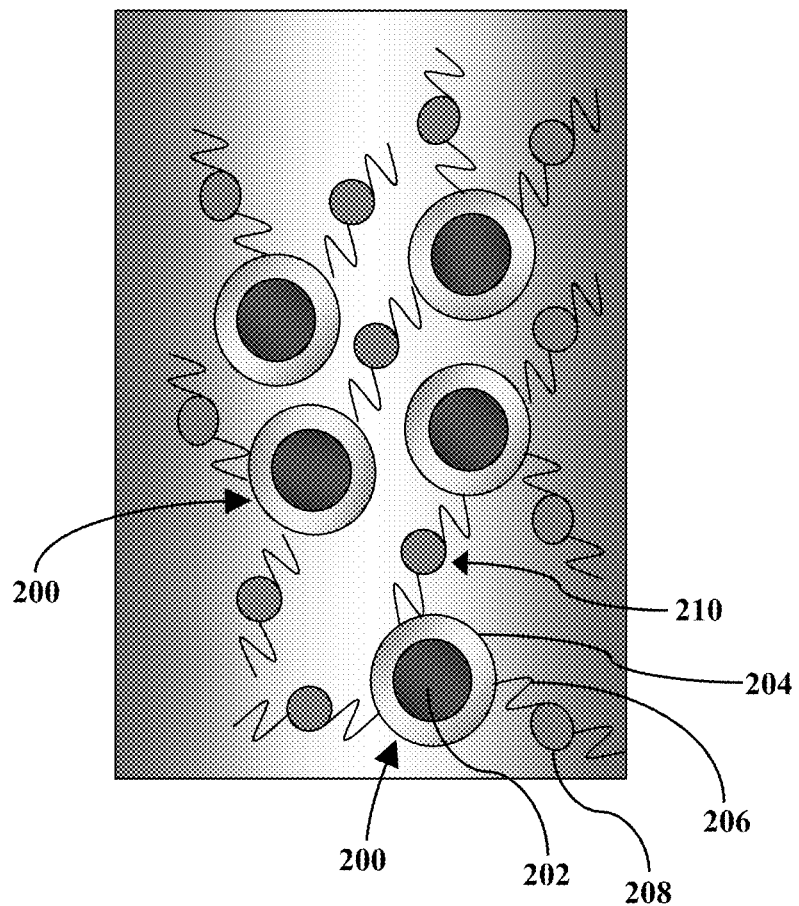
FIG. 2F shows schematically the structure of the $Fe_3O_4$—$SiO_2$/CdSe/ZnS nanocomposites according to one embodiment of the present invention.

FIGS. 2D and 2E show a EDX spectrum and a TEM image of the $Fe_3O_4$—$SiO_2$/CdSe/ZnS (IQ) nanocomposites, respectively. The structure of IQ nanocomposite was confirmed successfully by EDX and TEM analysis. The presence of Fe, O, Si, Cd, Se, Zn and S was affirmed from the characteristic peaks in the EDX spectrum shown in FIG. 2D. From the TEM image of the IQ nanocomposites shown in FIG. 2E, the darker regions represent the IO NPs, and the lighter regions attached to the exterior of the darker regions represent the smaller QDs of about 5 nm size. FIG. 2F shows schematically the structure of the IQ nanocomposites, which are shown as a group interfacing to each other.

The weight ratio between IOs and QDs in the final formulation is a key factor in developing future applications. Varying the iron oxide content from 0 to 51% caused a decrease in the fluorescence intensity by a factor of 100 [9]. At higher iron oxide concentrations, the quenching of the QDs is most likely the result of static and dynamic fluorescence quenching of the dots and strong absorption of the transmitted light by the iron oxide particles. In this study, an IO amount of about 20% was used, as the optical and magnetic properties of the nanocomposite were retained at this optimal levels. From the optical absorbance spectra shown in FIG. 2C, no significant changes in the absorbance intensity and position of the spectra between the water soluble QDs and the IQ nanocomposites were seen.

Figure 3:
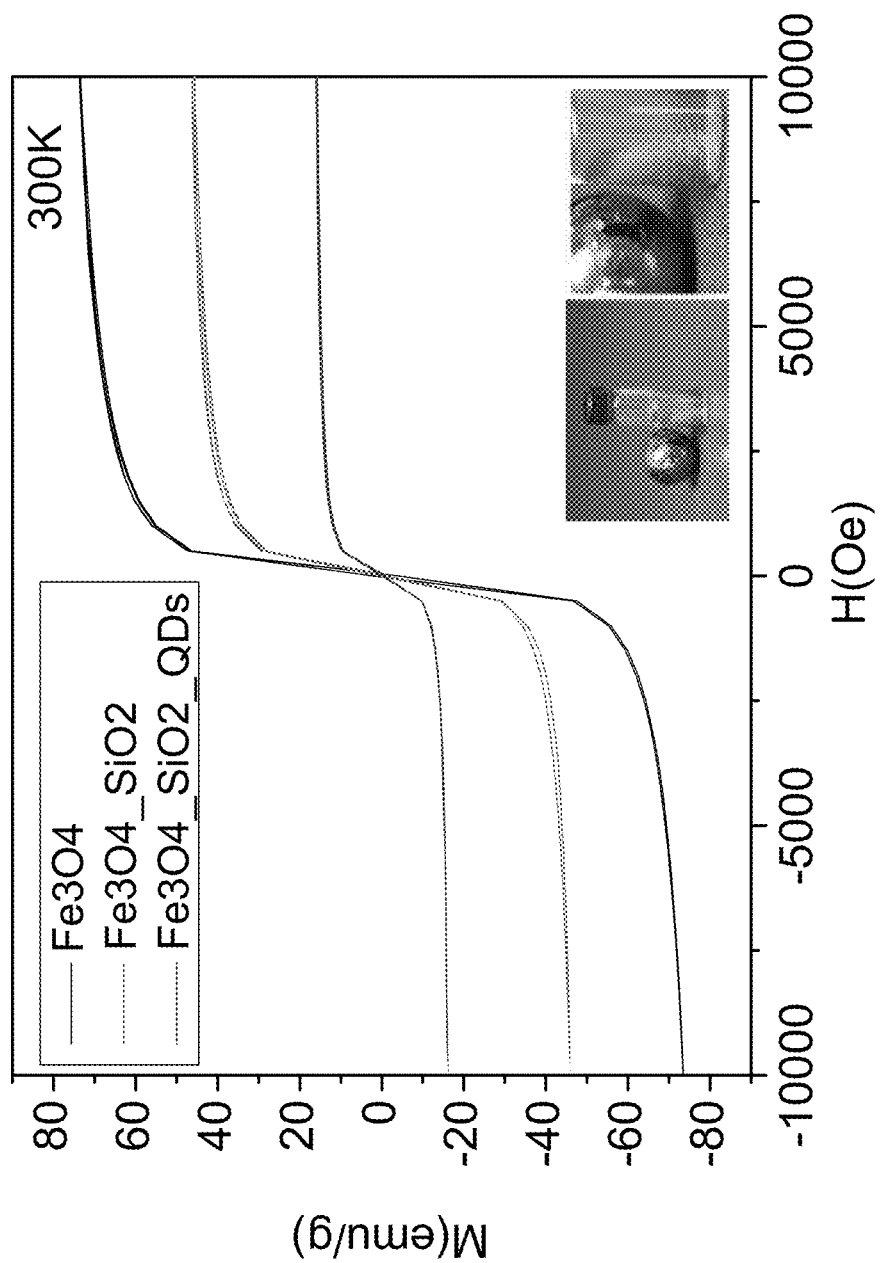
FIG. 3 shows hysteresis loops for the $Fe_3O_4$ nanoparticles (black line), $Fe_3O_4$—$SiO_2$ nanoparticles (red line), and the $Fe_3O_4$—$SiO_2$/CdSe/ZnS nanocomposites (blue line) measured at 300K, according to one embodiment of the present invention. The inserts show pictures of the $Fe_3O_4$—$SiO_2$/CdSe/ZnS nanocomposites separated by a magnetic ball in the solution.
Figure 4:
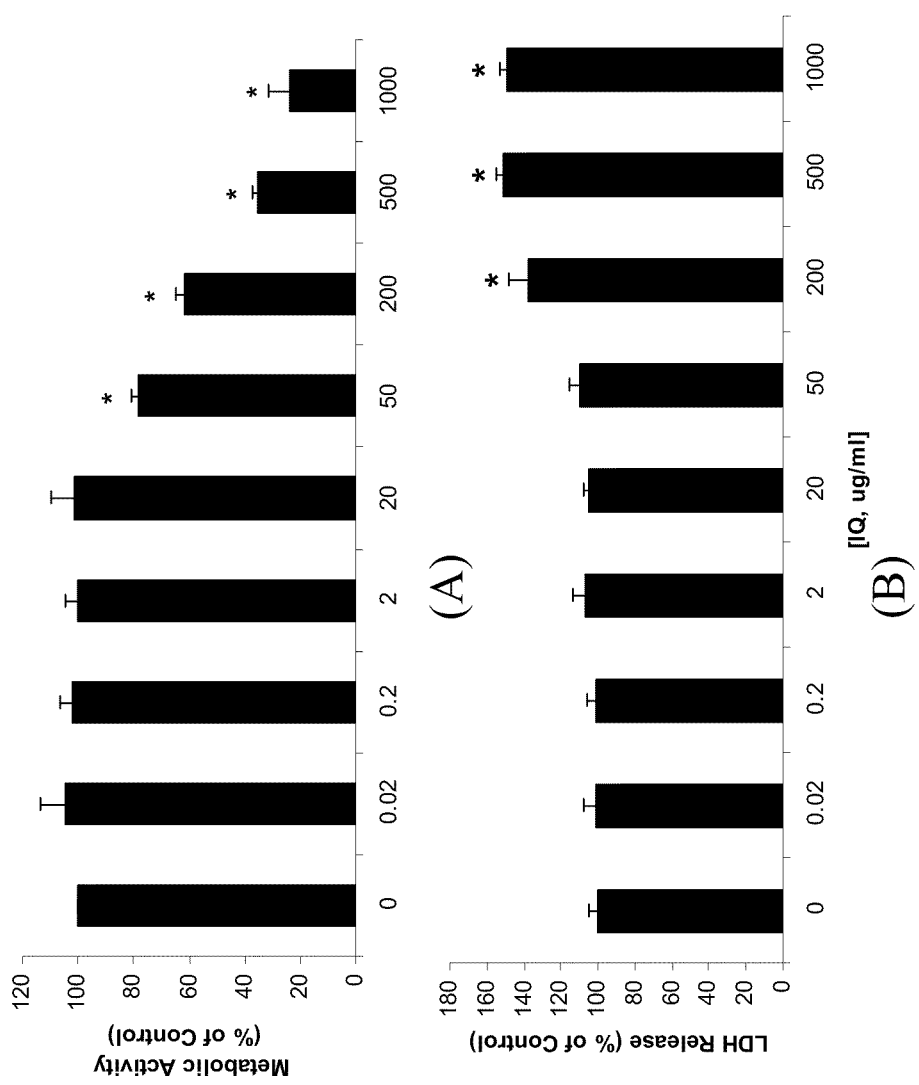
FIG. 4A summarizes the MTT results showing the effects of IQ composites on metabolic function of Panc 1 cells after 24 hours exposure according to one embodiment of the present invention.
FIG. 4B summarizes the LDH results showing the effects of IQ composites on Lactate Dehydrogenase of Panc-1 Cell after 24 hours exposure according to one embodiment of the present invention.

FIG. 3 shows hysteresis loops for the IO (black line), IOS (red line), and the IQ (blue line) nanocomposites measured at 300K, which exhibited ferromagnetic behavior. It should be noted that the magnetic properties of the IOS and IQ nanocomposites are provided by the IO particles. The saturation magnetization (Ms) decreased from 73.7 to 46.4 emu/g upon addition of a 4 nm $SiO_2$ shell to the nanocomposite morphology. Once the magnetic IOS particles were coated by the QD shells, the Ms values for the nanocomposites decreased to 15.4 emu/g. These IQ nanocomposites possess hysteretic properties when exposed to a time varying magnetic field, and this behavior leads to magnetically induced heating. The amount of heat generated per unit volume is given by the frequency multiplied by the area of the hysteresis loop. To further verify the magnetic properties of the IQ nanocomposites, an effective magnetic separation of the IQ nanocomposites from the solution was achieved using a moderate external magnetic field as shown in the insets of FIG. 3.

Example 3

Human Pancreatic Cancer Cell Culture

A human cancer cell line, Panc-1, was obtained from the American Type Culture Collection. The cells were maintained in Dulbecco's modified Eagle's medium (DMEM, GIBCO) supplemented with 10% fetal calf serum, 2% L-glutamine, 1% penicillin, and 1% streptomycin stock solutions. The media were changed every three days, and the cells were passaged by trypsinization before confluence.

MTT Assay

The colorimetric MTT (3-(4,5-dimethylthiazol-2-yl) 2,5-diphenyl tetrazolium bromide, Sigma) test was used to assess cell metabolic activity based on the ability of the mitochondrial succinate-tetrazolium reductase system to convert the yellow dye (MTT) to a blue-colored formazan. The metabolic activity of the cell is proportional to the color density formed. Briefly, following Panc-1 cell incubation with IQ for 24 hours, the media was aspirated and replaced with 90 µl of serum-free media. 10 µl of an MTT stock solution (5 mg/ml) was added to each well followed by incubation for 4 hours at 37° C. The supernatant was then removed and cells were lysed with 100 µl DMSO. Absorbance was recorded at 550 nm using a Synergy 2 microplate reader (Biotek, USA).

LDH Release Assay

Cell membrane integrity was measured using an LDH assay as the cell was targeted by chemicals. Lactate dehydrogenase (LDH) release activity was measured using a cytotoxicity detection kit from Roche Applied Science. Released LDH in culture supernatants was measured with a coupled enzymatic assay that resulted in the conversion of a tetrazolium salt (INT) into a red formazan product. Briefly, following cell incubation with IQ nanocomposites, 50 µL of supernatant was removed to another plate followed by the addition of 50 µL of substrate mix. The plate was covered with foil to protect it from light and was incubated for 30 minutes at room temperature followed by addition of 50 µL of stop solution to each well. Absorbance was recorded at 490 nm using a microplate reader (Biotek, USA).

Nanocomposites Incubation and RF Treatment of Cancer Cells

Human pancreatic cancer cells were incubated with 0.5, 0.83, 1.66 and 5 µg/mL of IQ nanocomposites in 35 mm culture dishes at a density of $0.5 \times 10^6$ cells/dish. The cultures were supplemented using DMEM Medium in a humidified incubator at 37° C. and 5% $CO_2$ for 24 hours. After incubation, the cells were washed with PBS to remove any nanocomposites that did not enter the cells. The cells were then subjected to 350 kHz, 5 kW, of radio frequency induction for time periods ranging from 2 to 10 minutes. Immediately after the RF treatment, cell images were captured by a Light Transmission Microscopy (Olympus BX51) to determine the percentage of dead and alive cells using 10×, 40×, and 100× magnification under UV radiation. The percentage of cells undergoing apoptosis was counted by confocal microscopy. Approximately 200-300 cells per treatment were counted to obtain statistically reliable percentages of dead cells.

Example 4

Cytotoxicity Studies

In theory, non-invasive RF treatment of malignant tumors at any site in the body should be possible. Such a treatment would require the presence of intracellular or intratumoral agents that release heat under the influence of an RF field. For such a novel RF treatment approach to be effective, it is necessary to identify agents that have little or no intrinsic cellular or tissue toxicity. Clearly, a non-invasive approach with the potential to treat many types of cancers effectively with minimal or no toxic side effects to normal cells would be highly beneficial[21].

MTT assays were used to evaluate the cytotoxicity of the IQ nanocomposites. In range finding studies, the IQ nanocomposites elicited concentration-dependent toxicity after 24 hours exposure like many other chemicals. FIG. 4A summarizes the MTT results showing the effects of IQ composites on metabolic function of Panc 1 cells after 24 hours exposure. As can be seen, no significant effect of IQ on Panc-1 cell viability was noted as the cells were exposed to 0-50 µg/ml of IQ for 24 hours. A previous study by Derfus and coworkers suggested that cytotoxicity of CdSe was correlated with the liberation of $Cd^{2+}$ from the nanoparticle lattice [23]. According to the present invention, the low toxicity of QDs is because the stable ZnS capping layer and MPA layer of the CdSe QDs significantly reduced the cytotoxicity. The effective coating prevents the CdSe QDs from being exposed to the intracellular environment thereby preventing $Cd^{2+}$ release.

Furthermore, LDH release assay, a traditional measurement of cell membrane damaged, was used to evaluate the cytotoxicity of IQ. FIG. 4B summarizes the LDH results showing the effects of IQ composites on lactate dehydrogenase (LDH) of Panc-1 Cell after 24 hours exposure. As can be seen, the cell membrane was not affected by the IQ at the concentration of 0-200 µg/ml after 24 hours exposure. However, significant effect of IQ was noted as the cells were exposed to higher concentration (above 200 µg/ml). Through these two studies, the dose of 20 µg/ml of the IQ was found safe for Panc-1 cells. Therefore, the maximum dose of 20 µg/ml was selected in the further therapeutic studies.

Example 5

In-vitro Therapeutic Studies
RF Treatment

Figure 5A:
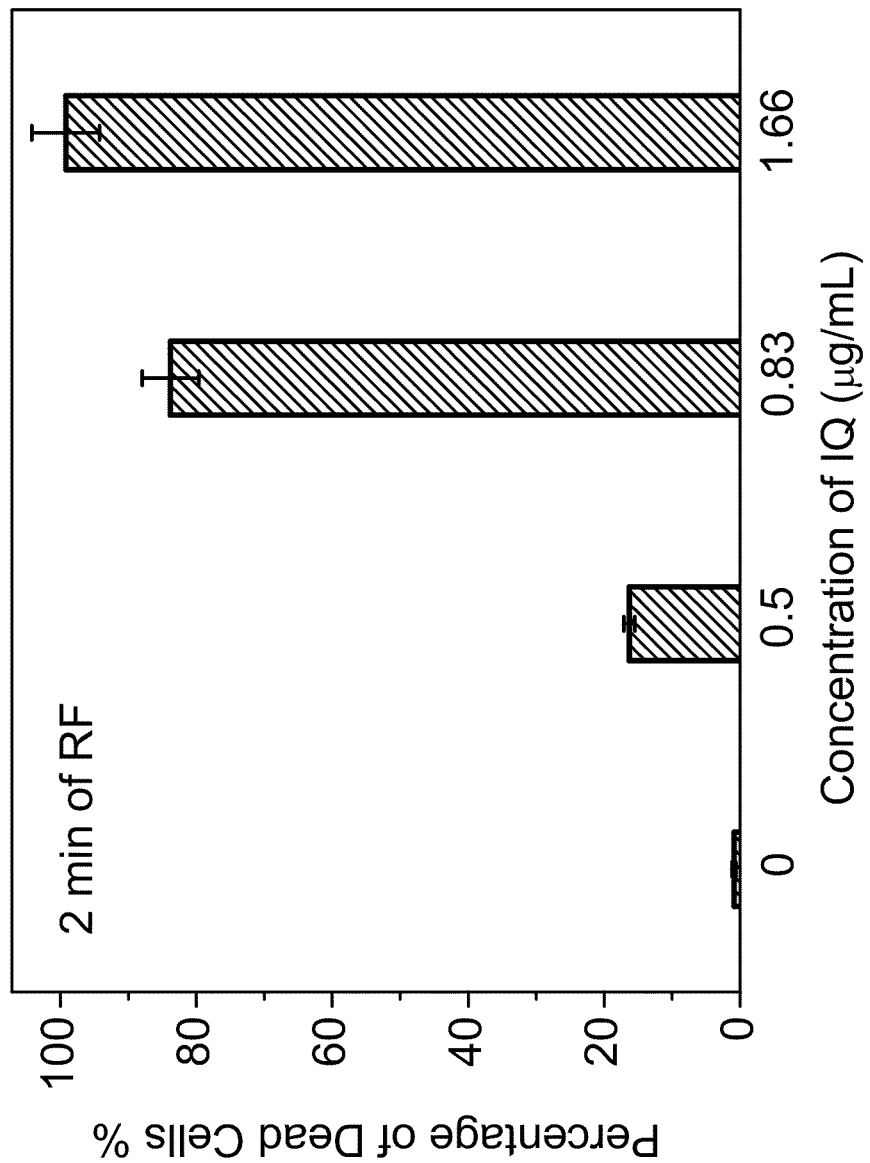
FIG. 5A shows the percentage of dead cells as a function of IQ concentration under RF treatment for 2 minutes according to one embodiment of the present invention.

Panc-1 cells cultured with various concentrations of nanocomposites were introduced inside a water-cooled coil coupled to a radiofrequency generator with a frequency of 350 kHz, which is far lower than what is commonly used (10 MHz to 300 GHz)[24]. The schematic diagram of this setup was shown in previous work from the inventors of the present invention [3]. Such low frequency radiation has the ability to penetrate the biological tissues efficiently and present a path of cancer treatment deep inside the body (e.g. at 400 kHz, field penetration into 15 cm of tissue is >99%)[25]. After the RF heating, the total number of dead and alive cells was immediately counted through visualization by fluorescence microscopy. FIG. 5A shows the percentage of dead cells as a function of IQ concentration under RF treatment for 2 minutes.

In order to confirm the biocompatibility of the nanocomposites, Panc-1 cell lines were cultured with 0.5-20 µg/ml of IQ and these cultures were subsequently analyzed for cell death. The results indicated that almost 99.5 to 99.0% of the total cultured cells were alive after one day of incubation, revealing almost no toxicity for the nanocomposites. Furthermore, as can be seen from FIG. 5A, RF radiation alone (corresponding to zero IQ concentration) induced hardly any effect to the Panc-1 cells with 99.1±0.3% of the cells alive after RF treatment.

FIG. 5A shows that, if the RF exposure time was kept constant, the death rate of the Panc-1 cells gradually increased with increasing nanocomposite concentrations. With only 2 minutes of RF exposure, 15.2-16.3% of cells were found dead by incubation with 0.5 µg/ml of nanocomposites. Even when the radiation time was extended to 10 min, there were still only 17.1-18.9% of cells found dead under this concentration. On the other hand, if the concentration was raised to 0.83 µg/ml, the percentage of dead cells increased to 82.2-83.8% of total cells counted. Further increasing the concentration of the nanocomposites to 1.66 µg/ml, it almost led to complete cell death as the percentage of dead cells increased to 98.7-99.2%. These results indicate that the IQ nanocomposite is an excellent RF absorber and induced cellular death in the a relatively short time and at a relatively low concentration in comparison to studies using other nanomaterials [3]. Moreover, for RF exposure times longer than 10 minutes, the percentage of dead cells increased rather slow (around 5-10% or less) depending on the type of NPs used in the experiment. As a result, if the exposure time was kept constant, the death rates of the cancer cells were found to be highly dependent on NP concentration. As shown in previous studies, when NP concentration was increased to 3.33 µg/mL, carbon coated Fe NPs (C—Fe) induced a death rate of almost 98.88-100% ($10^5$ cells in total) after only 2 minutes of RF exposure time[26]. But for the C—Co NPs, a significantly higher concentration (about 20 µg/mL) was required to cause the same effect [3]. These results can be explained by the fact that the RF electromagnetic radiation induces skin currents (heat) of various intensities into the different NPs, increasing their temperatures due to Ohmic effects [27].

Panc-1 Cancer Cell Imaging

Figure 5B:
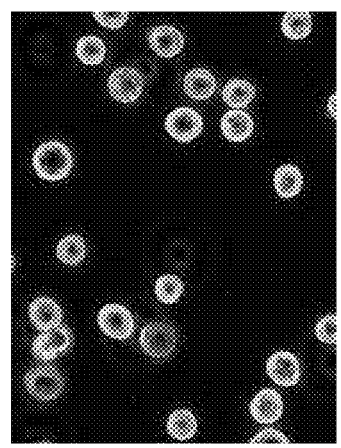
FIG. 5B shows a confocal microscopic image of the normal Panc-1 cells.
Figure 5C:
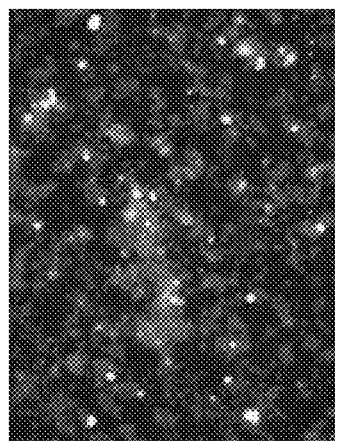
FIG. 5C shows a confocal microscopic image of the Panc-1 cells after incubation with the IQ nanocomposites for 24 hours according to one embodiment of the present invention.

One of the important areas in which fluorescent magnetic nanocomposites have demonstrated great potential is in cancer cells and tumor imaging. Confocal microscopic images of the living Panc-1 cells before and after incubation with the IQ nanocomposites are shown in FIGS. 5B and 5C, respectively. After 24 hours of incubating Panc-1 cells with IQ nanocomposites, fluorescent IQ was present everywhere the cells had grown. Some of them glowed very brightly when struck with ultraviolet radiation and photographed with a confocal microscope (FIG. 5C).

Figure 5D:
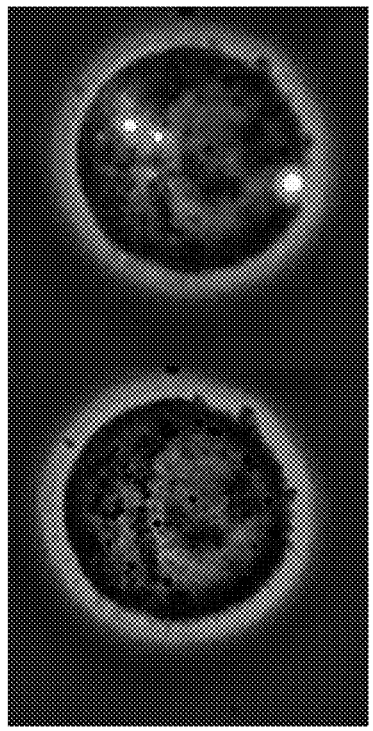
FIG. 5D shows confocal microscopic images of a cell after cellular uptake of the IQ nanocomposites according to one embodiment of the present invention, without (left) and with (right) UV radiation.
Figure 5E:
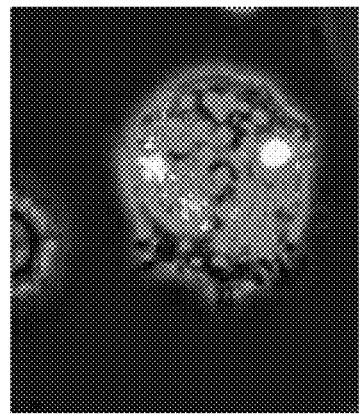
FIGS. 5E-5H show confocal microscopic images of cells showing cell shrinkage, membrane blebbing, and disintegration of the nuclear membranes resulted from the RF heating process, respectively, according to one embodiment of the present invention.
Figure 5F:
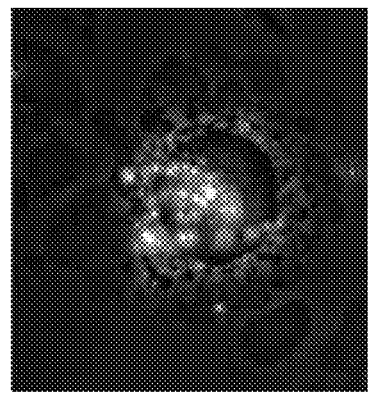
Figure 5G:
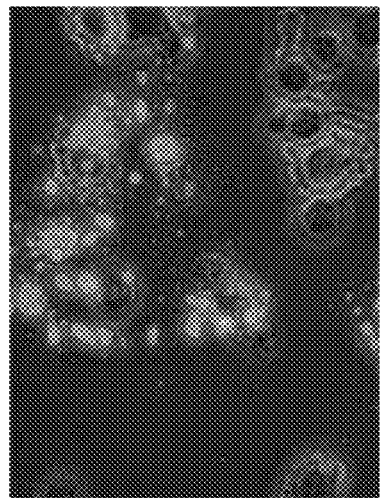
Figure 5H:
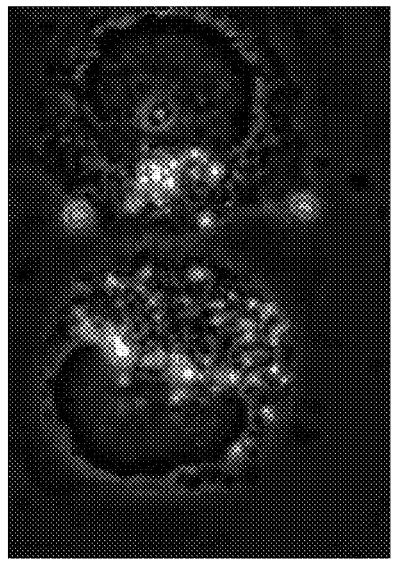

After cellular uptake of the IQ nanocomposites, the IQ nanocomposites were found to agglomerate around the nuclear membrane and a small number crossed the nuclear membrane into the nucleus. FIG. 5D shows confocal microscopic images of a cell after cellular uptake of the IQ nanocomposites, without (left) and with (right) UV radiation. Due to the localized RF heating provided by the IQ nanocomposites, the cells were found to go through an accelerated apoptotic process and consequent cellular decomposition. Conventional therapies such as radio frequency thermal therapy exert its therapeutic effect by indirectly promoting apoptosis [28]. This type of regimen induces apoptosis by causing DNA damage. In doing so, they stimulate apoptosis through the intrinsic pathway. FIGS. 5E-5H show confocal microscopic images of cells showing cell shrinkage, membrane blebbing, disintegration of the nuclear membranes, and apoptotic bodies resulted from the RF heating process. Therefore, these results indicate that such bifunctionalized nanocomposites not only can become strong RF absorbers, but can also help to label cell morphologies. They generate thermally localized cellular damages, such as DNA fragmentation and breakage of the cellular membranes, which can induce cell death and cancerous tissue apoptosis.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

List Of References

[1] (a) Peng, X.; Qian, X.; Mao, H.; Wang, A. Y.; Chen, Z.; Nie, S.; Shin, M., *Targeted magnetic iron oxide nanoparticles for tumor imaging and therapy*, International Journal of Nanomedicine, 2008, 3, 311-321.

(b) Lu, Y.; Yin, Y.; Mayers, B. T.; Xia, Y., *Modifying the Surface Properties of Superparamagnetic Iron Oxide Nanoparticles through A Sol-Gel Approach*, Nano Lett., 2002, 2, 183-186.

[2] Seo, W.; Lee, J.; Sun, X.; Suzuk, Y.; Mann, D.; Liu, Z.; Terashima, M.; Yang, P. C.; Mcconnell, M. V.; Nishimura D. G.; Dai, H., *FeCo/graphitic-shell nanocrystals as advanced magnetic-resonance-imaging and near-infrared agents*, Nature Materials, 2006, 5, 971-976.

[3] Xu, Y.; Mahmood, M.; Li, Z.; Dervishi, E.; Trigwell, S.; Zharov, V. P.; Ali, N.; Saini, V.; Biris, A. R.; Lupu, D.; Boldor D.; Biris, A. S., *Cobalt nanoparticles coated with graphitic shells as localized radio frequency absorbers for cancer therapy*, Nanotechnology, 2008, 19, 435102-435111.

[4] Pankhurst, Q. A.; Connolly, J.; Jones, S. K.; Dobson, J., *Applications of magnetic nanoparticles in biomedicine*, J. Phys. D: Appl. Phys. 2003, 36, R167-R181.

[5] Kalambur, V. S.; Han, B.; Hammer, B. E.; Shield T. W.; Bischof, J. C., *In vitro characterization of movement, heating and visualization of magnetic nanoparticles for biomedical applications*, Nanotechnology, 2005, 16, 1221-1233.

[6] Hergt, R.; Dutz, S.; Muller, R.; Zeisberger, M.; *Magnetic particle hyperthermia: nanoparticle magnetism and materials development for cancer therapy*, J. Phys.: Condens. Matter, 2006, 18, S2919-S2934.

[7] Tartaj, P.; Morales, M. P.; Veintemillas-Verdaguer, S.; Gonzalez-Carreno, T.; Serna, C. J., *Iron oxide MR contrast agents for molecular and cellular imaging*, J. Phys. D: Appl. Phys. 2003, 36, R182-R197.

[8] Kumar, R. V.; Koltypin, Y.; Cohen, Y. S.; Cohen, Y.; Aurbach, D.; Palchik, O.; Felner, I.; Gedanken. A., *Preparation of amorphous magnetite nanoparticles embedded in polyvinyl alcohol using ultrasound radiation*, J. Mater. Chem. 2000, 10, 1125-1129.

[9] Corr, S. A.; Rakovich, Y. P.; Gun'ko, Y. K.; *Multifunctional Magnetic-fluorescent Nanocomposites for Biomedical Applications*, Nanoscale Res. Lett., 2008, 3, 87-104.

[10] Szabo, D. V.; Vollath, D., *Template-assisted Self-assembly and Cobalt Doping of Ordered Mesoporous Titania Nanostructures*, Adv. Mater. 1999, 11, 1313.

[11] Bruchez, M.; Moronne, M.; Gin. P.; Weiss, S.; Alivisatos, A. P., *Semiconductor Nanocrystals as Fluorescent Biological Labels*, Science. 1998, 281, 2013-2018.

[12] Mattoussi, H.; Mauro, J. M.; Goldman, E. R.; Anderson, G. P.; Sundar, V. C.; Mikulec, F. V.; Bawendi, M. G.; *Self-Assembly of CdSe—ZnS Quantum Dot Bioconjugates Using an Engineered Recombinant Protein*, J. Am. Chem. Soc. 2000, 122, 12142-12150.

[13] Ballou, B.; Lagerholm, B. C.; Ernst, L. A.; Bruchez, M. P.; Waggoner, A. S., *Noninvasive Imaging of Quantum Dots in Mice*, Bioconjug. Chem., 2004, 15, 79-86.

[14] Michalet, X.; Pinaud, F. F.; Bentolila, L.; A.; Tsay, J. M.; Doose, S.; Li, J. J.; Sundaresan, G.; Wu, A. M.; Gambhir, S. S.; Weiss, S., *Quantum dots for live cells, in vivo imaging, and diagnostics*, Science. 2005, 307, 538-544.

[15] Montet, X.; Weissleder, R.; Josephson, L., *Imaging pancreatic cancer with a peptide-nanoparticle conjugate targeted to normal pancreas*, Bioconjugate Chemistry, 2006, 17, 905-911.

[16] Sun, Q.; Wang, Y. A.; Li, L.; Wang, D.; Zhu, T.; Xu, J.; Yang, C.; Li, Y., *Bright Multicoloured Light Emitting Diodes Based on Quantum Dots*, Nature Photonics, 2007, 1, 717-722.

[17] Blackman, B.; Battaglia, D.; Peng, X., *Bright and Water-Soluble Near IR-Emitting CdSe/CdTe/ZnSe Type-II/Type-I Nanocrystals, Tuning the Efficiency and Stability by Growth*, Chemistry of Materials. 2008, 20, 4847-4853.

[18] Woo, K.; Hong, J.; Choi, S.; Lee, H. W.; Ahn, J. P.; Kim, C. S.; Lee, S. W., *Easy synthesis and magnetic properties of iron oxide nanoparticles*, Chem Mater, 2004, 16, 2814-2818.

[19] Cheng, F. Y.; Su, C. H.; Yang, Y. S.; Yeh, C. S.; Tsai, C. Y.; Wu, C. L.; Wu, M. T.; Shieh, D. B.; *Characterization of aqueous dispersions of $Fe_3O_4$ nanoparticles and their biomedical applications*, Biomaterials. 2005, 26, 729-738.

[20] Yezhelyev, M. V.; Qi, L.; O'Regan, R. M.; Nie, S., Gao, X., *Proton-Sponge Coated Quantum Dots for siRNA Delivery and Intracellular Imaging. J. Am. Chem. Soc.,* 2008, 130, 9006-9012.

[21] Gannon, C. J.; Patra, C. R.; Bhattacharya, R.; Mukherjee P.; Curley, S. A., *Intracellular gold nanoparticles enhance non-invasive radiofrequency thermal destruction of human gastrointestinal cancer cells, Journal of Nanobiotechnology.* 2008, 6, 2-11.

[22] Fotakis, G.; Timbrell, J. A., *In vitro cytotoxicity assays: comparison of LDH, neutral red, MTT and protein assay in hepatoma cell lines following exposure to cadmium chloride, Toxicol Lett.,* 2006, 160, 171.

[23] Derfus, A. M.; Chan, W. C.; Bhatia, S. N., *Probing the cytotoxicity of semiconductor quantum dots, Nano Lett.* 2004, 4, 11-18.

[24] Leea, S.; Johnson, D.; Dunbar, K.; Dong, H.; Ge, X.; Kim, Y. C.; Wing, C.; Jayathilaka, N.; Emmanuel, N. C.; Zhou Q.; Gerber, H. L.; Tseng, C. C.; Wang, S., *2.45 GHz radiofrequency fields alter gene expression in cultured human cells, FEBS Lett.,* 2005, 579, 4829-4836.

[25] Young, J. H.; Wang, M. T.; Brezovich, I. A., *Frequency/depth-penetration considerations in hyperthermia by magnetically induced currents, Electron Lett.,* 1980, 16, 358-359.

[26] Xu, Y.; Mahmood, M.; Fejleh, A.; Li, Z., Watanabe, F.; Trigwell, S.; Little, R. B.; Kunets, V. P.; Dervish, E.; Biris, A. R.; Salamo, G. J.; Biris, A. S., *Carbon Covered Magnetic Nanomaterials and Their Application for Nanothermolysis of Cancer Cells, Nanomedicine.* 2009, under Review.

[27] Little, R. B.; Biris, A. R.; Lupu, D.; Xu, Y.; Li, Z.; Dervishi, E.; Biris, A. S., *On the dynamical ferromagnetic, quantum Hall, and relativistic effects on the carbon nanotubes nucleation and growth mechanism, Journal of Magnetism and Magnetic Materials,* 2008, 320, 540-547.

[28] Ghobrial, I. M.; Witzig, T. E.; Adjei, A. A., *Targeting apoptosis pathways in cancer, CA Cancer J. Clin.,* 2005, 55, 178-194.

What is claimed is:

1. A method of synthesizing magnetic oxide-quantum dot nanocomposites, comprising the steps of:
    (a) producing a plurality of magnetic oxide nanoparticles;
    (b) coating each of the plurality of magnetic oxide nanoparticles with a silica ($SiO_2$) shell terminated with at least one thiol group (—SH) via a sol-gel process;
    (c) producing a plurality of mercaptopropionic acid (MPA)-coated CdSe/ZnS quantum dots;
    (d) dissolving the plurality of MPA-coated CdSe/ZnS quantum dots in a liquid to form a first solution;
    (e) combining the plurality of $SiO_2$-coated and thiol-terminated magnetic oxide nanoparticles with the first solution to form a second solution; and
    (f) stirring the second solution for a first period of time such that a plurality of nanocomposites is formed, wherein each of the plurality of nanocomposites comprises:
        (i) at least one $SiO_2$-coated magnetic oxide nanoparticle, and (ii) at least one CdSe/ZnS quantum dot linked with the at least one $SiO_2$-coated magnetic oxide nanoparticle via the at least one thiol group.

2. The method of claim 1, wherein the liquid is water.

3. The method of claim 1, wherein the first period of time is about 12 hours.

4. The method of claim 1, further comprising the step of isolating the plurality of nanocomposites from the second solution by using a magnet.

5. The method of claim 1, wherein the plurality of magnetic oxide nanoparticles comprises a plurality of iron oxide ($Fe_3O_4$) nanoparticles.

6. The method of claim 5, wherein the step of producing a plurality of magnetic oxide nanoparticles is performed by the steps of:
    (a) mixing a first amount of ammonium ferrous sulfate and a second amount of iron chloride to form a third solution;
    (b) adding a third amount of sodium hydroxide into the third solution to form a fourth solution;
    (c) stirring the fourth solution for a second period of time such that the plurality of iron oxide ($Fe_3O_4$) nanoparticles is formed; and
    (d) isolating the plurality of $Fe_3O_4$ nanoparticles from the fourth solution.

7. The method of claim 6, wherein the step of stirring the fourth solution is performed under nitrogen protection.

8. The method claim 6, wherein the step of isolating the plurality of $Fe_3O_4$ nanoparticles from the fourth solution is performed by using a magnet.

9. The method of claim 1, wherein the step of producing a plurality of mercaptopropionic acid (MPA)-coated CdSe/ZnS quantum dots is performed by the steps of:
    (a) dissolving a plurality of CdSe/ZnS particles in a first amount of chloroform to form a fifth solution;
    (b) adding a second amount of mercaptopropionic acid (MPA) to the fifth solution to form a sixth solution;
    (c) sonicating the sixth solution for a third period of time such that the plurality of MPA-coated CdSe/ZnS quantum dots is formed; and
    (d) isolating the plurality of MPA-coated CdSe/ZnS quantum dots from the sixth solution.

10. The method of claim 9, wherein the third period of time is about 20 minutes.

11. The method of claim 9, wherein the step of isolating the plurality of MPA-coated CdSe/ZnS quantum dots from the sixth solution is performed via centrifugation and decantation.

12. The method of claim 11, wherein the step of stirring the sixth solution is performed in a 35° C. water bath.

* * * * *